United States Patent
Bertinetti et al.

(10) Patent No.: US 10,149,952 B2
(45) Date of Patent: *Dec. 11, 2018

(54) CONTINUOUS POSITIVE AIRWAY PRESSURE DEVICE WITH USER INTERFACE

(71) Applicant: ResMed Limited, Bella Vista, New South Wales (AU)

(72) Inventors: Mark Bertinetti, Sydney (AU); David Peter Wawrzonek, Marmong Point (AU); Phoebe Katherine Hill, Sydney (AU); Rohan Neil Primrose, Sydney (AU); Heike Thiele, Munich (DE); Alexander Virr, Gosford (AU); Andrew Roderick Bath, Sydney (AU); Sandra Robyn Curtis, Blue Mountains (AU); Andrew Mikael Price, Sydney (AU)

(73) Assignee: RESMED LIMITED, Bella Vista (AU)

( * ) Notice: Subject to any disclaimer, the term of this patent is extended or adjusted under 35 U.S.C. 154(b) by 571 days.

This patent is subject to a terminal disclaimer.

(21) Appl. No.: 14/726,859

(22) Filed: Jun. 1, 2015

(65) Prior Publication Data

US 2015/0290406 A1 Oct. 15, 2015

Related U.S. Application Data

(63) Continuation of application No. 12/734,469, filed as application No. PCT/AU2008/001638 on Nov. 5, 2008, now Pat. No. 9,072,848.

(30) Foreign Application Priority Data

Nov. 5, 2007 (AU) ................................ 2007906080
Nov. 26, 2007 (AU) ................................ 2007906444

(Continued)

(51) Int. Cl.
A61M 16/16 (2006.01)
A61M 16/00 (2006.01)
(Continued)

(52) U.S. Cl.
CPC .... A61M 16/0003 (2014.02); A61M 16/0051 (2013.01); A61M 16/0057 (2013.01);
(Continued)

(58) Field of Classification Search
CPC .......... A61M 16/0057; A61M 16/0066; A61M 16/0069; A61M 16/08; A61M 16/0841;
(Continued)

(56) References Cited

U.S. PATENT DOCUMENTS 4,408,172 A 10/1983 Perdue
4,531,233 A 7/1985 Nelson
(Continued)

FOREIGN PATENT DOCUMENTS

CN 1809397 A 7/2006
CN 101024106 A 8/2007
(Continued)

OTHER PUBLICATIONS

Extension of Time Granted mailed Jun. 25, 2015, together with Notice of Opposition to Grant of Patent (Section 21) and an Application Under Section 21(2) (Proviso) for an Extension of the Period for Giving Notice of Opposition filed Jun. 24, 2015 in New Zealand Application No. 615069 (4 pages).
(Continued)

Primary Examiner — Annette Dixon
(74) Attorney, Agent, or Firm — Nixon & Vanderhye, P.C.

(57) ABSTRACT

A continuous positive airway pressure (CPAP) device to non-invasively treat a sleep disordered breathing disorder of a user may include a humidifier indicator backlight config-
(Continued)

ured to indicate operation of a humidifier and a heated tube, the humidifier indicator backlight having an on state and an off state, a first backlit color and a second backlit color, and a first brightness and a second brightness, and the humidifier indicator backlight being configured to change between the first backlit color and the second backlit color and/or between the first brightness and the second brightness in response to user adjustment of a humidifier setting and/or a heated tube setting.

25 Claims, 13 Drawing Sheets

(30) Foreign Application Priority Data

Sep. 17, 2008 (AU) ................................ 2008904835
Oct. 1, 2008 (AU) ................................ 2008905107

(51) Int. Cl.
*A61M 16/10* (2006.01)
*A61M 16/06* (2006.01)
*A61M 16/20* (2006.01)

(52) U.S. Cl.
CPC ...... *A61M 16/0069* (2014.02); *A61M 16/024* (2017.08); *A61M 16/06* (2013.01); *A61M 16/1095* (2014.02); *A61M 16/16* (2013.01); *A61M 16/20* (2013.01); *A61M 2016/0027* (2013.01); *A61M 2016/0036* (2013.01); *A61M 2205/18* (2013.01); *A61M 2205/3334* (2013.01); *A61M 2205/36* (2013.01); *A61M 2205/505* (2013.01); *A61M 2205/52* (2013.01); *A61M 2205/584* (2013.01); *A61M 2205/8206* (2013.01); *A61M 2205/8237* (2013.01); *A61M 2205/8262* (2013.01)

(58) Field of Classification Search
CPC ............ A61M 16/107; A61M 16/1075; A61M 16/1085; A61M 16/1095; A61M 16/16; A61M 16/164; A61M 2016/0036; A61M 2205/3368; A61M 2205/52; A61M 2230/10; A61M 2230/18; A61M 2230/60; A61M 2230/63; B22F 2003/033; B22F 3/03; B30B 11/04; B62J 2099/0026; B62J 6/003; B62J 99/00; F04D 25/166; F04D 29/052; G01C 22/002; G01C 23/00; G06F 1/163; G06F 3/0202; G06F 3/021; G06F 3/0216; G06F 3/0219; G06F 3/0238; G09G 2320/041; G09G 3/3406; H04M 1/22; H04M 2250/12
USPC ............ 128/203.17, 203.27, 204.18, 204.22, 128/204.24; 235/145 R, 1 R; 261/130; 345/102; 715/866
See application file for complete search history.

(56) References Cited

U.S. PATENT DOCUMENTS

| | | | |
|---|---|---|---|
| 4,621,632 A * | 11/1986 | Bartels | A61M 16/1075 128/203.17 |
| 4,647,219 A | 3/1987 | Figler et al. | |
| 4,867,152 A | 9/1989 | Kou | |
| 5,237,987 A | 8/1993 | Anderson et al. | |
| 5,270,689 A | 12/1993 | Hermann | |
| 5,398,676 A | 3/1995 | Press et al. | |
| 5,627,531 A | 5/1997 | Posso et al. | |
| 5,647,346 A | 7/1997 | Holscher | |
| 5,881,723 A | 3/1999 | Wallace et al. | |
| 5,931,160 A | 8/1999 | Gilmore et al. | |
| 6,005,299 A | 12/1999 | Hengst | |
| 6,188,407 B1 | 2/2001 | Smith et al. | |
| 6,237,846 B1 * | 5/2001 | Lowell | G06F 1/163 235/1 R |
| 6,349,724 B1 * | 2/2002 | Burton | A61M 16/0057 128/204.18 |
| 6,360,741 B2 | 3/2002 | Truschel | |
| 6,369,838 B1 | 4/2002 | Wallace et al. | |
| 6,410,871 B1 | 6/2002 | Rarbach | |
| 6,543,449 B1 | 4/2003 | Woodring et al. | |
| 6,554,260 B1 | 4/2003 | Lipscombe et al. | |
| 6,773,398 B2 | 8/2004 | Ogasawara et al. | |
| 6,895,963 B1 | 5/2005 | Martin et al. | |
| 7,100,608 B2 | 9/2006 | Brewer et al. | |
| 7,106,955 B2 | 9/2006 | Thudor et al. | |
| 7,314,046 B2 | 1/2008 | Schroeder et al. | |
| 7,942,380 B2 | 5/2011 | Bertinetti et al. | |
| 8,122,883 B2 | 2/2012 | Banner et al. | |
| 8,161,404 B2 | 4/2012 | Kolletzki | |
| 2002/0022973 A1 | 2/2002 | Sun et al. | |
| 2003/0062045 A1 | 4/2003 | Woodring et al. | |
| 2004/0140189 A1 | 7/2004 | Ruegenberg | |
| 2004/0189722 A1 * | 9/2004 | Acres | B62J 6/003 715/866 |
| 2005/0039305 A1 | 2/2005 | Chirumbolo | |
| 2005/0179638 A1 * | 8/2005 | Seo | G09G 3/3406 345/102 |
| 2006/0130836 A1 | 6/2006 | Wixey et al. | |
| 2007/0062533 A1 | 3/2007 | Choncholas et al. | |
| 2007/0169776 A1 | 7/2007 | Kepler et al. | |
| 2007/0175480 A1 | 8/2007 | Gradon et al. | |
| 2007/0193582 A1 | 8/2007 | Kwok et al. | |
| 2007/0215155 A1 | 9/2007 | Marx et al. | |
| 2007/0249331 A1 | 10/2007 | Sinivaara et al. | |
| 2008/0000477 A1 | 1/2008 | Huster et al. | |
| 2008/0041380 A1 | 2/2008 | Wallace et al. | |
| 2008/0072896 A1 | 3/2008 | Setzer et al. | |
| 2008/0072900 A1 | 3/2008 | Kenyon et al. | |
| 2008/0097175 A1 | 4/2008 | Boyce et al. | |
| 2008/0099017 A1 | 5/2008 | Bordewick et al. | |
| 2008/0167082 A1 | 7/2008 | Gurevich et al. | |
| 2008/0185009 A1 | 8/2008 | Choncholas et al. | |
| 2008/0202527 A1 | 8/2008 | Hutchinson et al. | |
| 2009/0113238 A1 | 4/2009 | Liu et al. | |
| 2009/0223514 A1 | 9/2009 | Smith | |
| 2010/0229867 A1 | 9/2010 | Bertinetti et al. | |
| 2011/0164002 A1 | 7/2011 | Hill et al. | |
| 2012/0055476 A1 | 3/2012 | Choncholas | |

FOREIGN PATENT DOCUMENTS

| | | |
|---|---|---|
| DE | 19 747 284 | 4/1999 |
| DE | 197 47 284 A1 | 4/1999 |
| EP | 0 102 332 | 3/1989 |
| EP | 0 314 305 | 5/1989 |
| EP | 2 098 260 | 9/2009 |
| GB | 2 338 420 | 12/1999 |
| JP | 2000-322185 | 11/2000 |
| JP | 2001-337774 | 12/2001 |
| WO | 1997/06843 | 2/1997 |
| WO | 1997/006843 | 2/1997 |
| WO | 1998/011574 | 3/1998 |
| WO | 98/41267 | 9/1998 |
| WO | WO 01/32069 A2 | 5/2001 |
| WO | 2008/056993 | 5/2008 |
| WO | 2009/059359 | 5/2009 |
| WO | WO 2011/056080 | 10/2010 |

OTHER PUBLICATIONS

Notice of the Second Office Action dated Feb. 8, 2014 for Chinese Application No. 200980137016.4 (14 pages).
Decision of Rejection w/English Translation dated Mar. 18, 2014 for Japanese Application No. 2011-626356 (4 pages).
Notice of Opposition dated Feb. 25, 2014 for New Zealand Application No. 611919 (2 pages).

(56) References Cited

OTHER PUBLICATIONS

Notice of Reasons for Rejection w/English Translation dated Aug. 27, 2013 for Japanese Application No. 2011-526356 (5 pages).
Patent Examination Report No. 1 for Australian Application No. 2009295267, dated Sep. 5, 2013 (3 pages).
Final Office Action dated Dec. 20, 2013 corresponding to U.S. Appl. No. 12/998,085 (47 pages).
Respironics Heated Humidifier M Series User Manual 2006.
New Zealand First Examination Report for Application No. 611919 dated Jun. 20, 2013, 2 pages.
New Zealand Further Examination corresponding to NZ Application No. 591807 dated Jun. 20, 2013, 2 pages.
English Translation of Notice on the First Office Action for corresponding CN Application No. 200980137016, dated May 28, 2013, 4 pages.
Examination Report for corresponding New Zealand Application No. 591807, dated Aug. 16, 2012, 2 pages.
International Search Report for PCT/AU2009/001231, dated Jan. 28, 2010.
U.S. Appl. No. 12/998,085, filed Mar. 16, 2011 (pending).
Respironics RemStar Pro User Manual dated Feb. 28, 2006 referenced in Office Action as NPL1.
Screeen dump from http://directhomemedical.com/ds400-mseries-remstar-pro-epap0machine.html referenced in Office Action as NPL2.
International Search Report for PCT/AU2008/001638, dated Dec. 23, 2008.
Statement of Case issued in New Zealand Application No. 611919 dated Jun. 23, 2014, (10 pages).
Amended Notice of Opposition to Grant of Patent issued in New Zealand Application No. 611919, dated Jun. 23, 2014, (4 pages).
Supplementary Search Report issued in related European Application No. EP 08 84 7722 dated Nov. 7, 2017, 10 pages.

* cited by examiner

CONTINUOUS POSITIVE AIRWAY PRESSURE DEVICE WITH USER INTERFACE

CROSS REFERENCE TO RELATED APPLICATIONS

This application is a continuation of U.S. application Ser. No. 12/734,469, filed May 4, 2010, which is the U.S. national phase of International Application No. PCT/AU2008/001638 filed Nov. 5, 2008, which designated the U.S. and claims the benefit of Australian Provisional Application No. 2007906080 filed on Nov. 5, 2007, Australian Provisional Application No. 2007906444, filed Nov. 26, 2007, Australian Provisional Application No. 2008904835, filed Sep. 17, 2008 and Australian Provisional Application No. 2008905107, filed Oct. 1, 2008, each of which is incorporated herein in its entirety.

BACKGROUND OF THE INVENTION

1. Field of the Invention

The present invention relates to ventilation systems used to treat respiratory disorders or diseases. Ventilation systems includes invasive and non-invasive ventilation, Continuous Positive Airway Pressure (CPAP), Bilevel therapy and treatment for sleep disordered breathing (SDB) conditions such as Obstructive Sleep Apnea (OSA), and for various other respiratory disorders and diseases. The ventilation system can be used in emergency situations to provide rapid invasive or non-invasive respiratory ventilator assistance, or in general to provide non-invasive ventilator assistance.

2. Description of Related Art

Ventilation of a patient involves the delivery of a breathable gas (typically ambient air to which a complementary gas such as oxygen can be added) pressurised above atmospheric pressure to a patient via a conduit, and a mask or tracheotomy tube. The main aim of mechanical ventilation is to simply assist with breathing.

There are many conditions that require assisted and/or controlled ventilation of the patient. It is common to use ventilator devices for diseases where mechanical ventilation is needed, for example in neuromuscular disease where volume controlled ventilation is required. These devices may also be used for other respiratory diseases or disorders, such as for the continuous positive airway pressure (CPAP) treatment of obstructive sleep apnea.

For either application of assisted and/or controlled ventilation, the pressure of the gas delivered to patients can be constant level, bi-level (in synchronism with patient breathing) or auto-adjusting in level. Further, some troubles require feeding the patient with a controlled volume of breathable gas, such as for neuromuscular patients. Throughout this specification reference to ventilation system is intended to incorporate a reference to any one of, or combinations of, these forms of pressurised gas supply.

Ventilation is commonly used in emergency situations to provide effective respiratory assistance to people in respiratory distress. For example to victims in car accidents, heart attacks, drug overdoses or other distressing situations. Under emergency conditions medical paramedics commonly provide ventilation using manual ventilation devices such as a bag valve mask. A bag valve ventilation technique functions in a similar manner to the well known mouth-to-mouth resuscitation technique except the air being blown into patients lungs comes from the bag rather than an individuals lungs. In contrast a mechanical ventilator uses a machine to blow the air into a patients lung. Mechanical ventilators are rarely used in emergency situations due to their larger size, complexity and time required to set-up such devices.

Ventilation can be provided as invasive ventilation or non-invasive ventilation. Invasive ventilation typically includes the use of a Laryngeal mask; endotracheal tube or intubation or Cricothyroidotomy whilst non-invasive ventilation generally includes the use of a mask or nasal prongs.

During emergency situations it has been proven that the sooner medical treatment is initiated the higher the rate of survival. Many countries now employ a rapid response emergency paramedic, particularly motorcycle paramedics, to provide quicker emergency support than that provided by current ambulance services. A rapid response emergency paramedic commonly operates as a single man unit. Thus, size, weight and time to set-up ventilation are critical to the successful treatment and ultimate survival of the victim.

Mechanical ventilators are predominantly used in hospitals or for long term care as they are generally large and complex. However, there have been some portable mechanical ventilators developed. U.S. Pat. No. 4,651,731 Vicenzi et al. 1987 discloses a portable fully self contained single patient ventilator/resuscitator device that has minimal features and modes of ventilation to reduce the cost and complexity so that minimally trained personnel can operate the device. Another such device is the Smiths Medical—Pneupac VR1, a compact design that is very simple.

U.S. Pat. No. 6,848,444 Smith et al. 2005 discloses a patient ventilator integrated with state-of the-art commercial off the shelf physiologic sensors and a digitally controlled feedback system for automated monitoring and regulation for use by the first responder to provide on-scene critical life-saving support through more advanced levels of care during the critical minutes after an injury and during evacuation.

There still remains a need for smaller, lighter, more portable like support devices that are easy to use and quick to set up so they can be operated in emergency type situations where time is very important.

None of these prior art devices provides an entirely satisfactory solution to the provision of emergency ventilation to the patient, nor to ease of construction and use requirements required under such emergency or rapid response conditions.

SUMMARY OF THE INVENTION

One aspect of the present invention aims to provide an alternative ventilation system arrangement which overcomes or ameliorates the disadvantages of the prior art, or at least provides a useful choice.

In one form, the invention provides a ventilator device for use in emergency situations.

Another aspect of the invention relates to a multifunction control member, e.g., a dial, for selection of functions/modes and parameters within those functions/modes, e.g., for use in a ventilator device or a device to deliver positive pressure therapy to a patient. The control member may be finger manipulatable in first and second manners to allow scrolling and selection functions. The control member is specifically suited for use in ventilator devices, although the control member could be used in other applications as well.

In one aspect of the present invention, there is provided a ventilator comprising a display screen to display a plurality of ventilator functions/modes and a plurality of parameters associated with at least one of said ventilator functions/modes, and a finger-operable dial to select from the plurality of ventilator functions/modes and parameters, the dial being manipulatable in a first manner to scroll between said parameters, and being manipulatable in a second manner to select one of the parameters.

In one aspect of the present invention, there is provided a method to control a ventilator comprising displaying a plurality of ventilator functions/modes and a plurality of parameters associated with at least one of said ventilator functions/modes; and using a single finger-operable dial, selecting from the plurality of ventilator functions/modes and parameters, the dial being manipulated in a first manner to scroll between said parameters, and being manipulated in a second manner to select one of the parameters.

In another aspect of the present invention, there is provided a ventilator device comprising a blower to generate pressurized gas in a pressure range suitable for treatment of a breathing disorder; and a user interface having a display screen to display at least one menu and a sub-menu including a plurality of parameters associated with said menu, and a multi-function control member (e.g., a single dial) operable in a first manner to scroll between said parameters and in a second manner, different from the first manner, to select one or more of the parameters. The first manner of operation of the control member may include rotation of the control member, while the second manner of operation of the control member may include touching, pressing, and/or depression of the control member.

These and other aspects of the invention will be described in the following detailed description of example embodiments.

BRIEF DESCRIPTION OF THE DRAWINGS

Further preferred embodiments or examples of the invention will now be described with reference to the accompanying drawings, in which.

DETAILED DESCRIPTION OF EXAMPLE EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute an additional embodiment.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise, comprised and comprises where they appear.

Ventilator Device

FIGS. 1-4 illustrate an embodiment of a ventilator device 10 to enhance an emergency paramedic's efforts in emergency situations. In general the ventilator is a small, light and portable. The ventilator device can also have more traditional uses, such as for clinical or in-home CPAP or Bilevel Therapy for SDB conditions such as OSA.

In an embodiment the ventilator provides pressure and volume controlled ventilation on victims requiring emergency resuscitation and or emergency life-support. The ventilator device is applicable for use on both adult and pediatric patients requiring a tidal volume of approximately 50 ml up to a spontaneous respiratory rate of 80 breaths per minute, both invasively and non-invasively.

In one example, the ventilator device will have an operating range of −5 to +40 degrees centigrade and may function within an altitude of 0 to 3000 meters above sea level. In one example, the ventilator weighs less than 3 kg, more preferably less than 2 kg.

In one embodiment the ventilator device provides a system that combines a re-breather (closed circuit) system with a ventilator—that ultimately conserves oxygen consumption allowing greater product-use time whilst "in-the-field". The ventilator device may be used by rapid response paramedics, such as motorcycle paramedics or flying medical personnel or military units or other similar situations that require urgent response ventilation.

Figure 1:
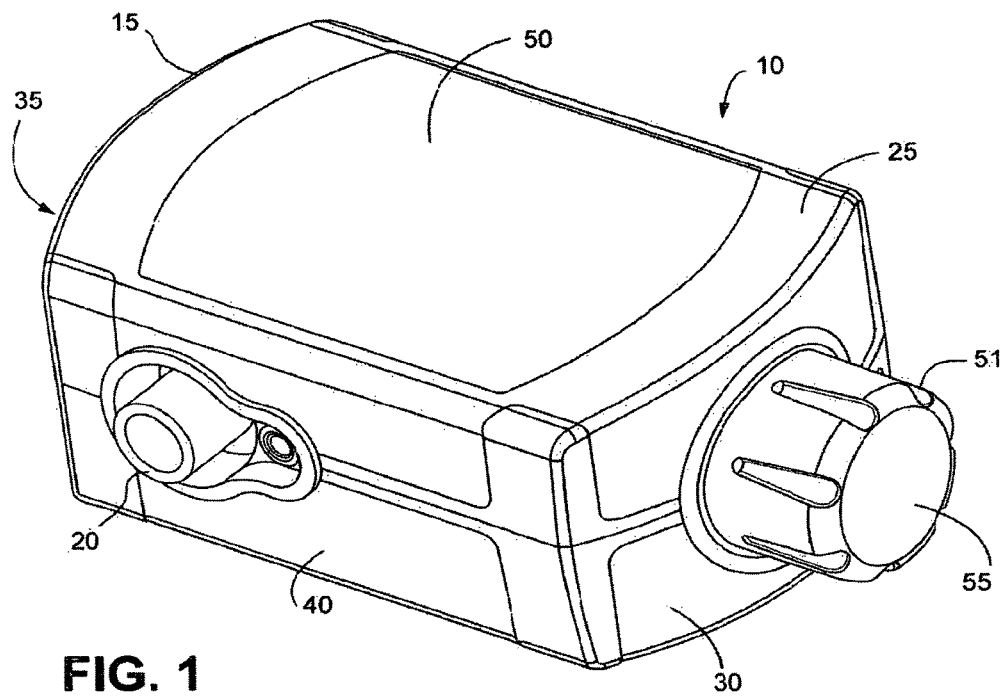
FIG. 1 shows a front side perspective view of an embodiment of a ventilator device according to an example embodiment according to the invention.
Figure 2:
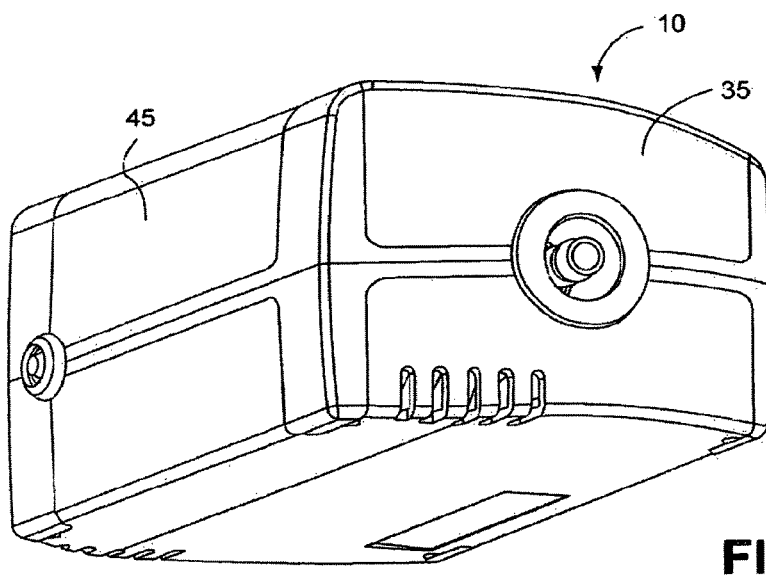
FIG. 2 shows a rear side perspective view of the ventilator device in FIG. 1.
Figure 3:
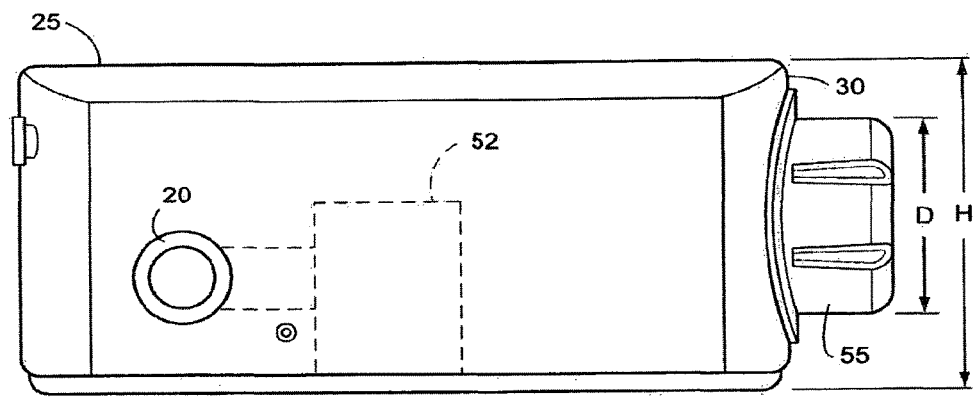
FIGS. 3 and 4 show side and top views, respectively, of a ventilator device similar to that shown in FIG. 1.

As can be seen in FIG. 1 the ventilator device 10 includes a main housing 15 that defines an inlet and an outlet 20. Outlet 20 is adapted for connection to an air-delivery tube that can deliver gas to the patient via a patient interface. The air delivery tube may be heated, which may be referred to herein as a "heated tube". Housing 15 includes or contains a blower 52 (e.g., motor with one or more impellers) that can generate pressurized gas typically in the range of 2-30 cm $H_2O$.

Ventilator device 10 may also include a humidification function. The humidification function can be built into ventilator device 10, or the humidification function can be provided as part of a separate component that is attached to or otherwise in communication with the ventilator device, in which the gas from the outlet of the ventilator device is delivered to the humidifier part. The humidifier part can be controlled in conjunction with the processor or controller of the ventilator device, or it may have a separate control or processor.

Housing 15 includes a top face 25 and a plurality of side faces, including side faces 30, 35 and front and rear faces 40, 45. Top face 25 includes a user interface with a screen 50 and a control member, e.g., a single dial 55, for selection of ventilator functions and parameters. The dial rotates to enable different parameters to be viewed or highlighted. Also, dial 55 provides or allows a push in selection function to select the desired parameter.

Figure 4:
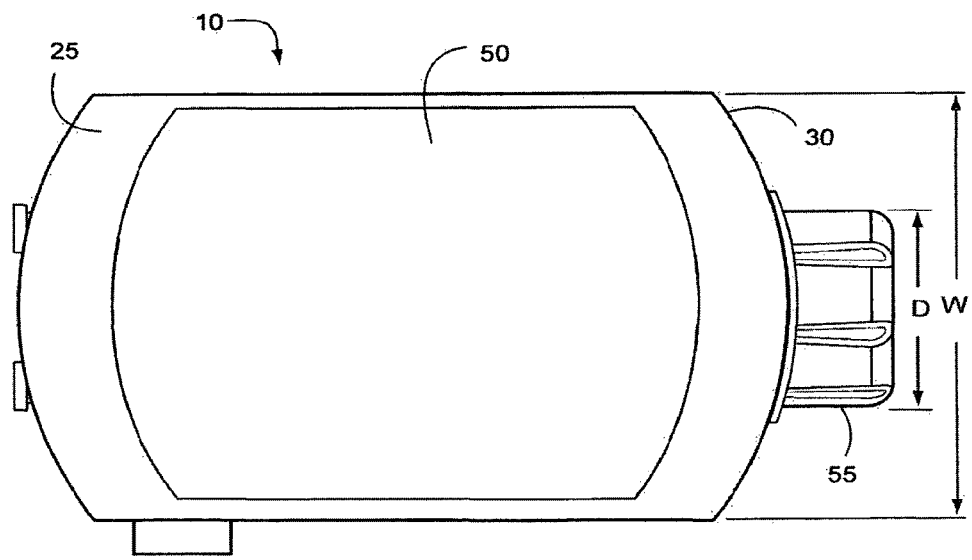

Top face 25 and screen 50 are structured such that screen 50 occupies the vast majority of available area of top face, e.g., 50%/50-100% or about 75-95%. Dial 55 is designed to be rather large, and may include one or more grooves 51 to facilitate handling. Dial 55 may be structured such that its diameter D is more than ½ (or about 70-90%) the height H of side face 30 (see FIG. 3). In addition, diameter D is about 40-60% (or about half) the width W of top face 25 (FIG. 4). Of course, the screen and dial can be positioned on different faces, e.g., dial can be on front or rear face, or even on top face 25 adjacent screen 50.

The ventilator device may be used with any known patient interface device such as a non-vented mask, nasal mask, full face mask, nasal prongs, nozzles or puffs, tracheal cuff, an uncuffed tracheotomy or other such interfaces. The ventilator may also be compatible with anti-bacterial filters.

In one example, the ventilator system is compatible with an expiratory valve such as those disclosed in PCT/IB2005/001454 and PCT/EP2006/061989, the contents of which are incorporated herein in their entirety.

User Interface

Figure 4A:
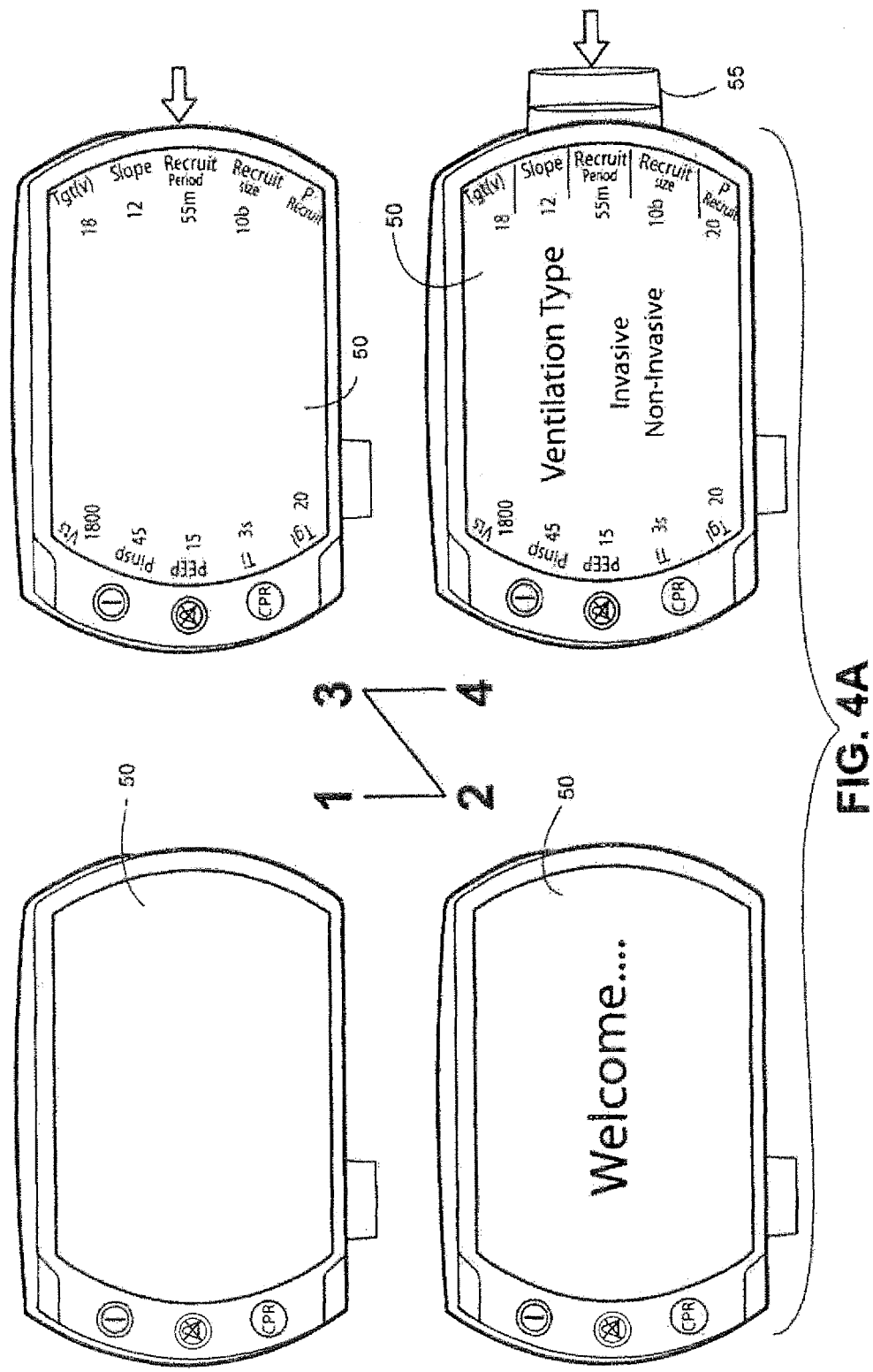
FIGS. 4A to 4F illustrate an embodiment of the user interface system and set-up for the ventilator device.
Figure 4B:
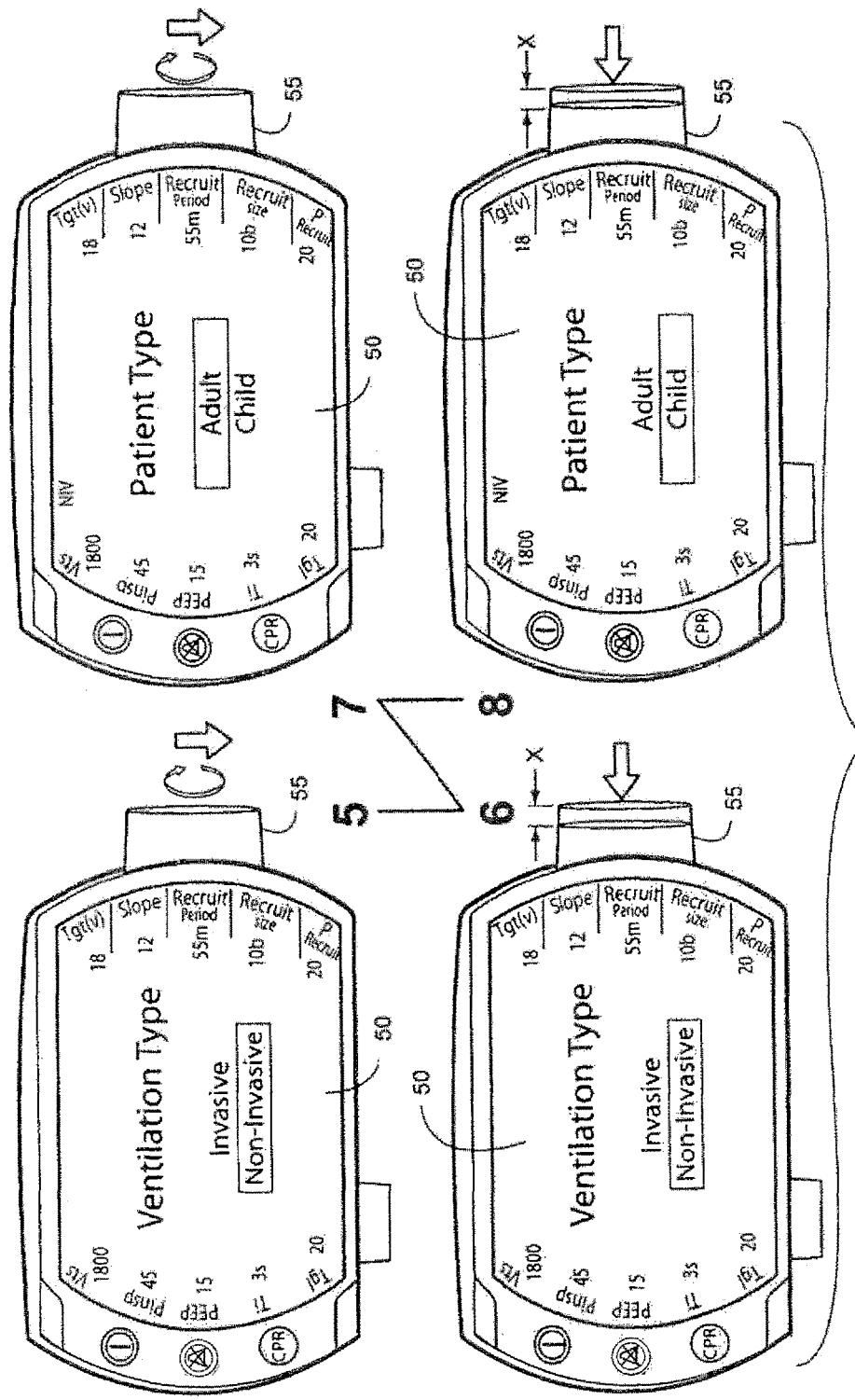
Figure 4C:
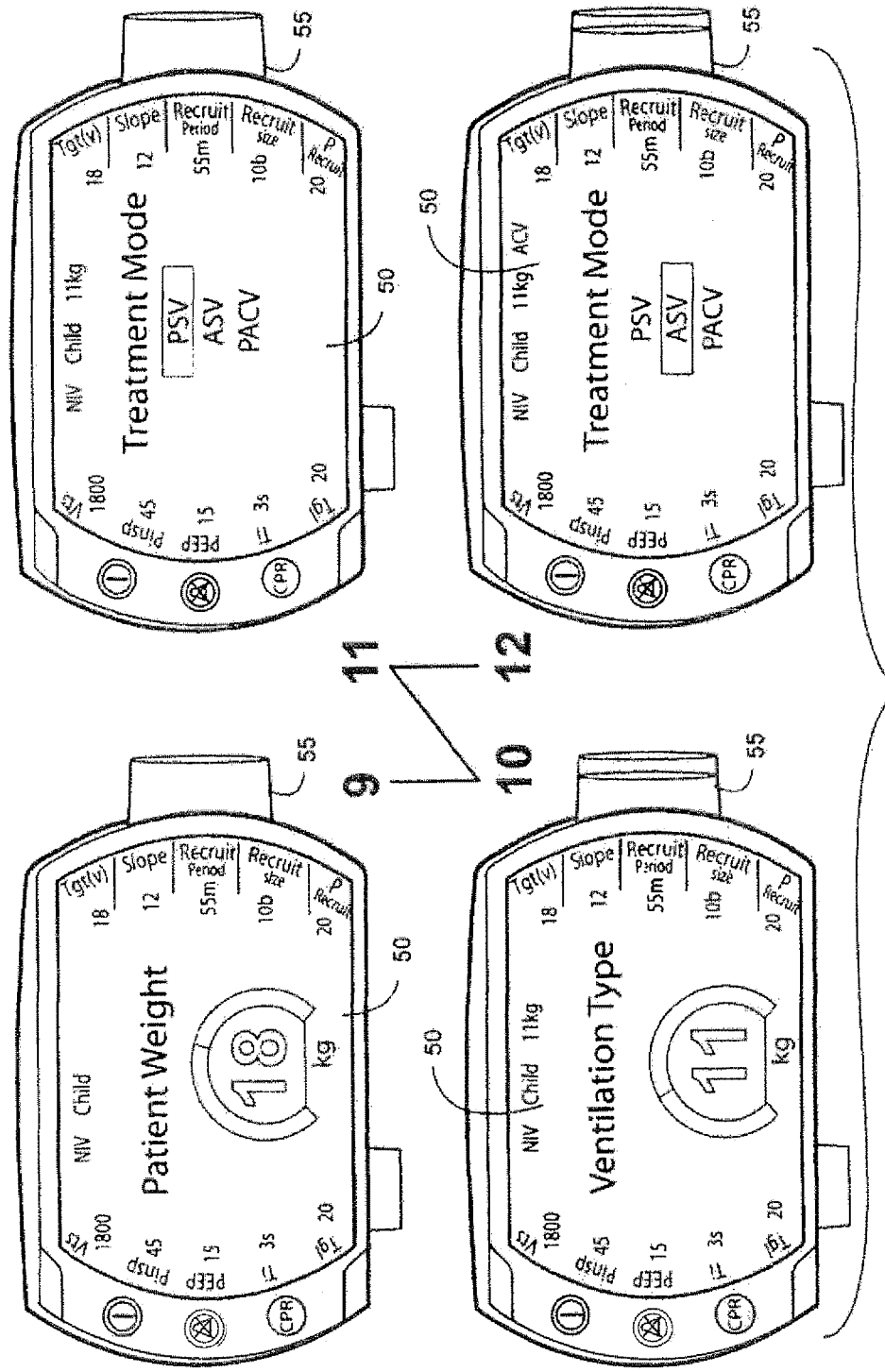
Figure 4D:
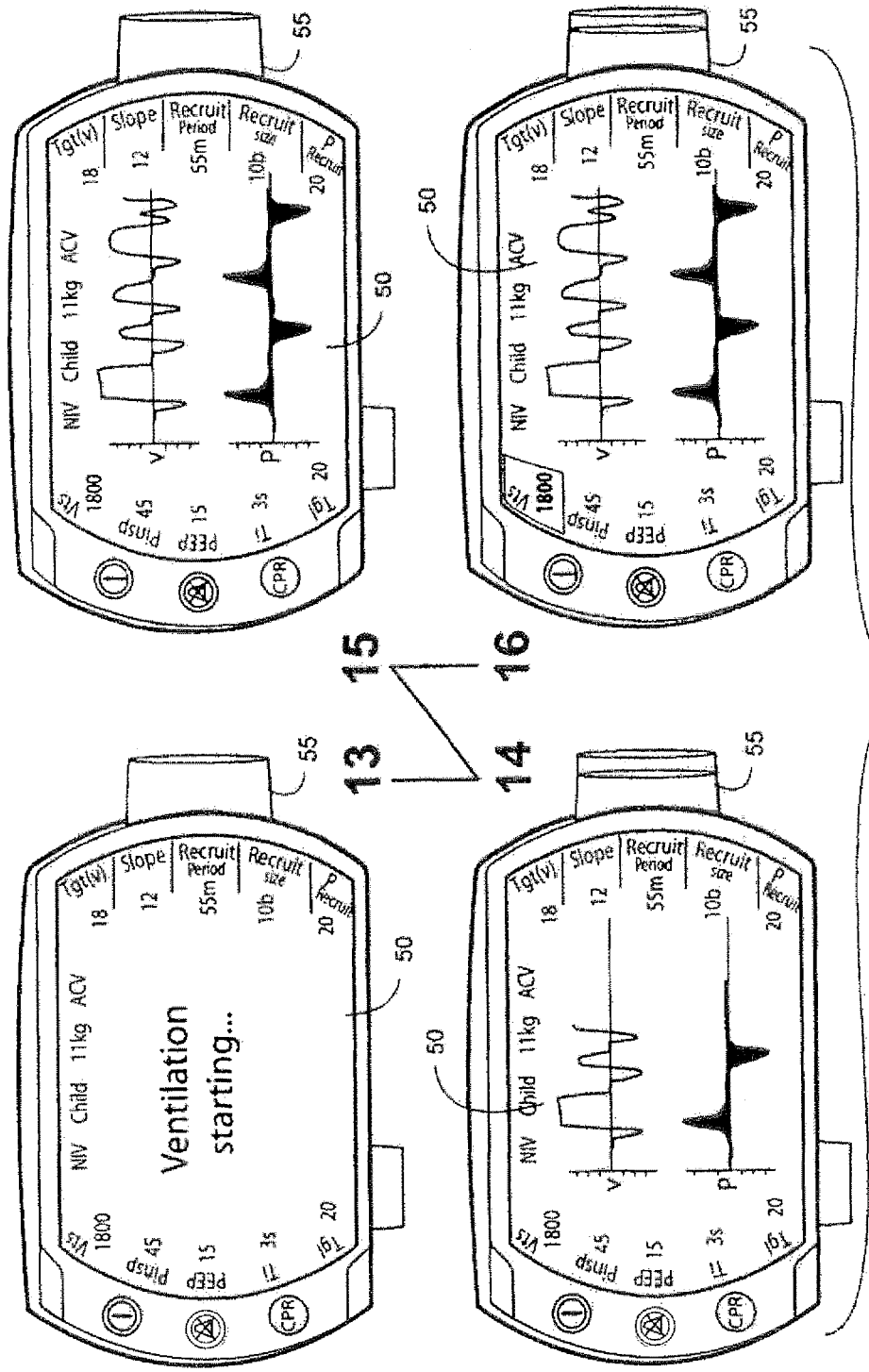
Figure 4E:
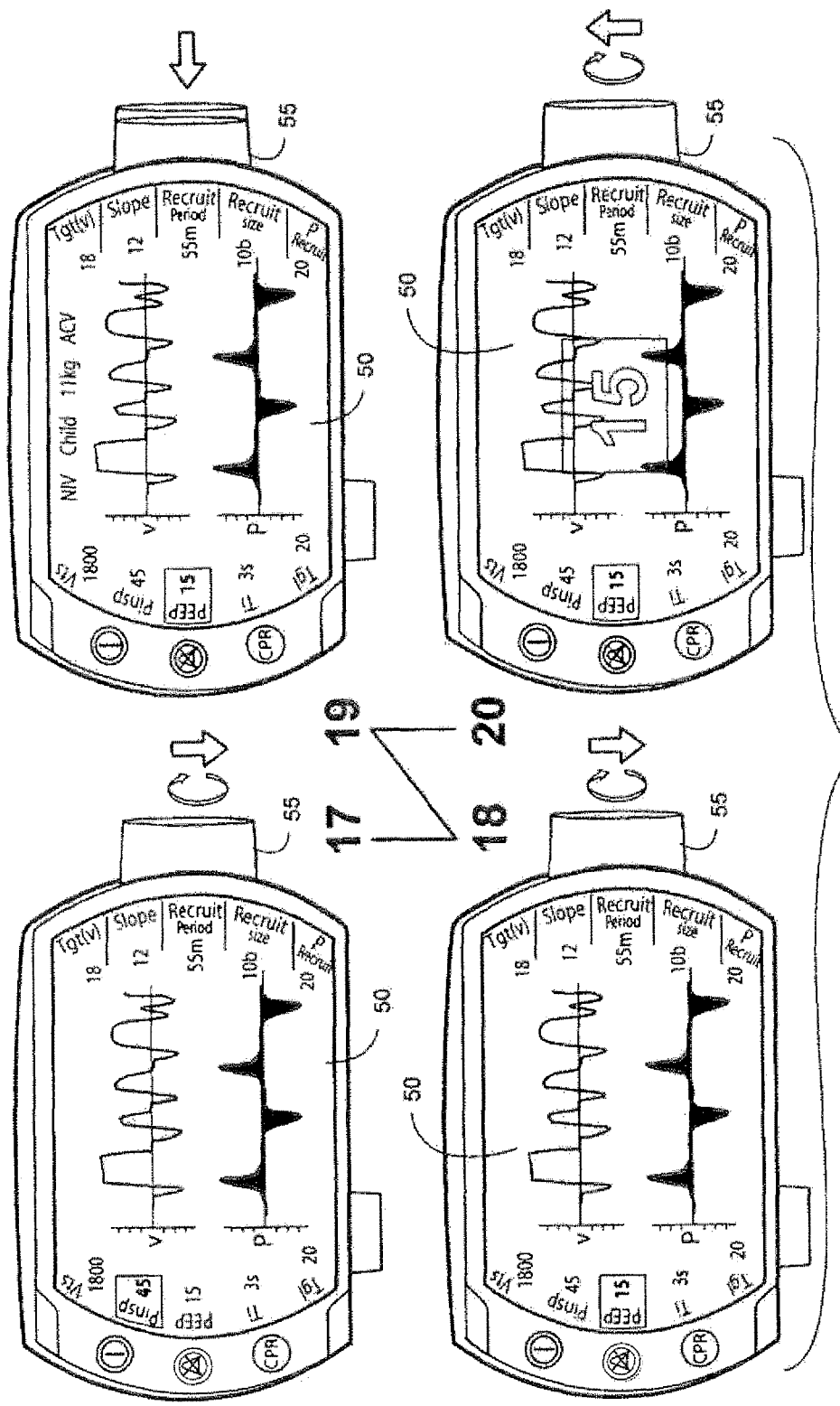
Figure 4F:
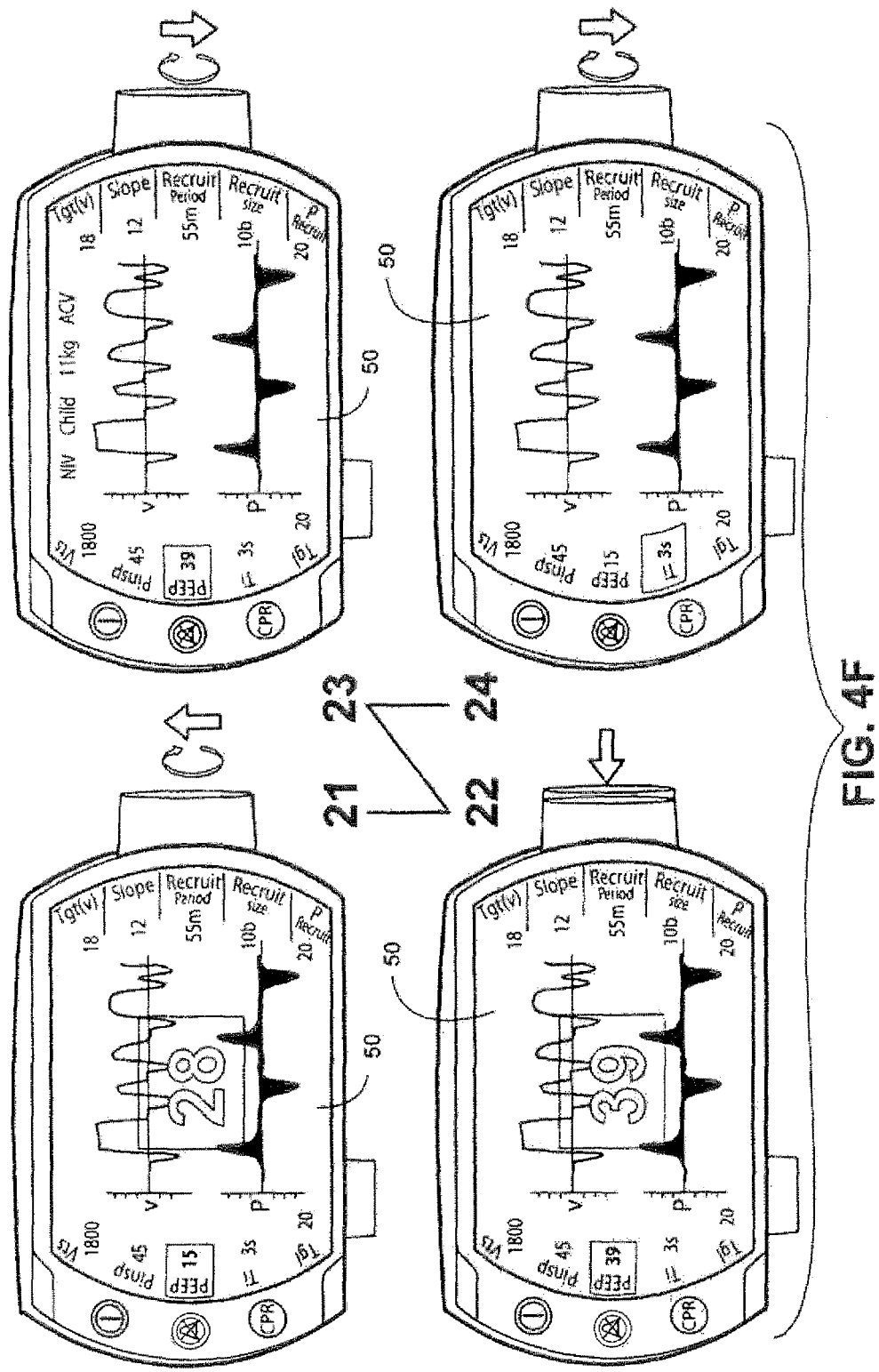

FIGS. 4A to 4F show an embodiment of the user interface system and how the ventilator can be easily controlled. The user interface allows for simple selection of the required ventilation functions/modes and parameters, and effective monitoring. For example, FIGS. 4A-4C show several ventilator functions/modes (e.g., "Ventilation Type", "Patient Type", "Patient Weight", and "Treatment Mode") and associated parameters ("Invasive" or "Non-Invasive", "Adult" or "Child", patient weight in kg, and "PSV", "ACV" or "PACU"), respectively. FIGS. 4D-4F plot pressure and volume curves once ventilation has commenced, for monitoring and warning or alerting purposes. The data may be recorded by the ventilator device to be provided to medical staff at a later time. The data may be recorded using an internal memory or external memory device such as a data card or via wireless transmission.

In another embodiment the user interface of the ventilator device uses a simple ultra slimmed down symbol based user interface based on a traffic light system that seeks to improve ease-of-use issues, as well as speed-to-set-up by providing only the necessary feedback symbols to indicate ventilation quality, using red, orange and green to indicate fix—immediate attention required, caution and good, respectively. In chaotic situations the universally recognised symbols would provide immediate accurate enough feedback for effective ventilation to be administered.

In this example, the primary objective is to maintain and sustain life—the quality of ventilation is secondary but critical. The red, orange, green feedback symbols speed up set-up time as no reading or time lag is required to identify satisfactory performance. Furthermore, the ventilator may include three basic modes of operation . . . one-touch (auto) mode, simplified (tutorial) mode and advanced (ICU—fully operational) mode. The one-touch mode incorporates a one-touch on or off operation button for immediate ventilation to be started. In another embodiment autonomous synchrony with the patient may be achieved by using a standardised setting criteria similar to that in U.S. Pat. No. 6,976,467 B1 where a relationship between height and ventilatory requirements has been established.

The different modes of operation would allow for an untrained person to commence ventilation using the one touch simplified on or off mode and then advance to the tutorial based post set-up mode for fine-tuning parameters to be set and adjustment based on the feedback from the traffic-light system. After transportation and stabilization to the hospital has been achieved, or a main gas and electrical supply can be utilized to allow the ventilator to provide further features. In this way adequate monitoring and detailed data feedback can be established for the clinician to adjust ventilation requirements. Additional features and modes can be accessed upon the necessary detection of a display, power supply and gas supply.

One embodiment of the ventilator device 10 includes rotatable/depressable dial 55 as indicated in FIGS. 4A to 4F. The dial allows for multiple functions to be incorporated into a single dial, rather than two or more separate dials or the combination of a dial and a switch and/or mode button. The dial includes at least two operating configurations. In a first configuration the dial is retracted within the ventilator device and in a second configuration the dial is extended out from the ventilator device. The dial may have one or multiple extension levels from the ventilator device. In FIG. 4A, screens 1 to 3 show the dial in the first configuration, in which the dial is retracted into the ventilator. In the first configuration the user interface may be locked such that no changes in settings can occur. For example the keypad does not function. FIG. 4A screen 4 and FIGS. 4B and 4C show the dial in the second configuration with the dial extended. The ventilator device is unlocked when the dial is in the second configuration to allow changes in the settings and to provide an active keypad. In the second configuration the dial may be rotated to scroll through user interface menus present in the device.

In one example, the dial provides a tactile and/or visual feedback to user when a setting is being altered. A second (e.g., harder) spring may be present in the dial that requires a stronger force to compress the dial to the retracted position returning the dial to the first configuration. A fastener, e.g., mechanical (catch) magnetic, etc., maintains the dial in the first configuration.

In one example, the dial may have a biasing mechanism, e.g., one or more springs, and mechanical details that enable a selected function. The biasing mechanism (e.g., a small damped, spring) may provide for a short compression requiring a small compression force to select a desired function. FIG. 4B screens 5-8 illustrate how the dial may function. Screens 6 and 8 of FIG. 4B show the dial 55 being depressed a small amount x to select the desired parameter.

In operation, the ventilator includes a control system (having a processor controlled or operated by software, hardware and/or firmware or the like) that is configured to walk the user through a number of functions which have options and therefore require user input. In this mode, the ventilator screen automatically displays the various functions/modes (or menus) and the parameters (sub-menu) are scrolled with usually one, but possibly more, of the parameters being selected using the dial. For example, once the ventilator function/mode is displayed, e.g., "Ventilation Type" in FIG. 4A (screen 4), the user manipulates the dial, e.g., by touching, pressing and/or depressing it, such that the sub-menu is displayed in which case the user can scroll (e.g., by rotating the dial) between the parameters "Invasive" or "Non-Invasive". The user selects between the sub-menu choices by further manipulation of the dial (e.g., touching, pressing and/or depressing). The dial can be manipulated in two different manners to scroll through functions/modes and/or parameters (via rotation of the dial) and select the desired one(s) (via depression of the dial). Of course, other modes of manipulation of the dial are contemplated.

In the example illustrated, the control system is programmed or set up to sequentially display all functions/modes in automatic fashion. However, the control system can also be set up to allow the user to scroll through various functions/modes and select them, similar to how parameters are scrolled and selected.

The dial may be rotated to select the desired parameter within a given function or mode, for example "Non-Invasive" in the "Ventilation Type" mode (FIG. 4B, screen 6) or "Child" in the "Patient Type" mode (FIG. 4B, screen 8), then the dial face is pressed, touched or depressed, e.g., in minimal amount x, as indicated in FIG. 4B screens 6 and 8, to select the desired parameter. If compressed or depressed, the dial returns to the extended position or second configuration, as shown in FIG. 4B screen 7.

Alternative User Interface

Figure 5:
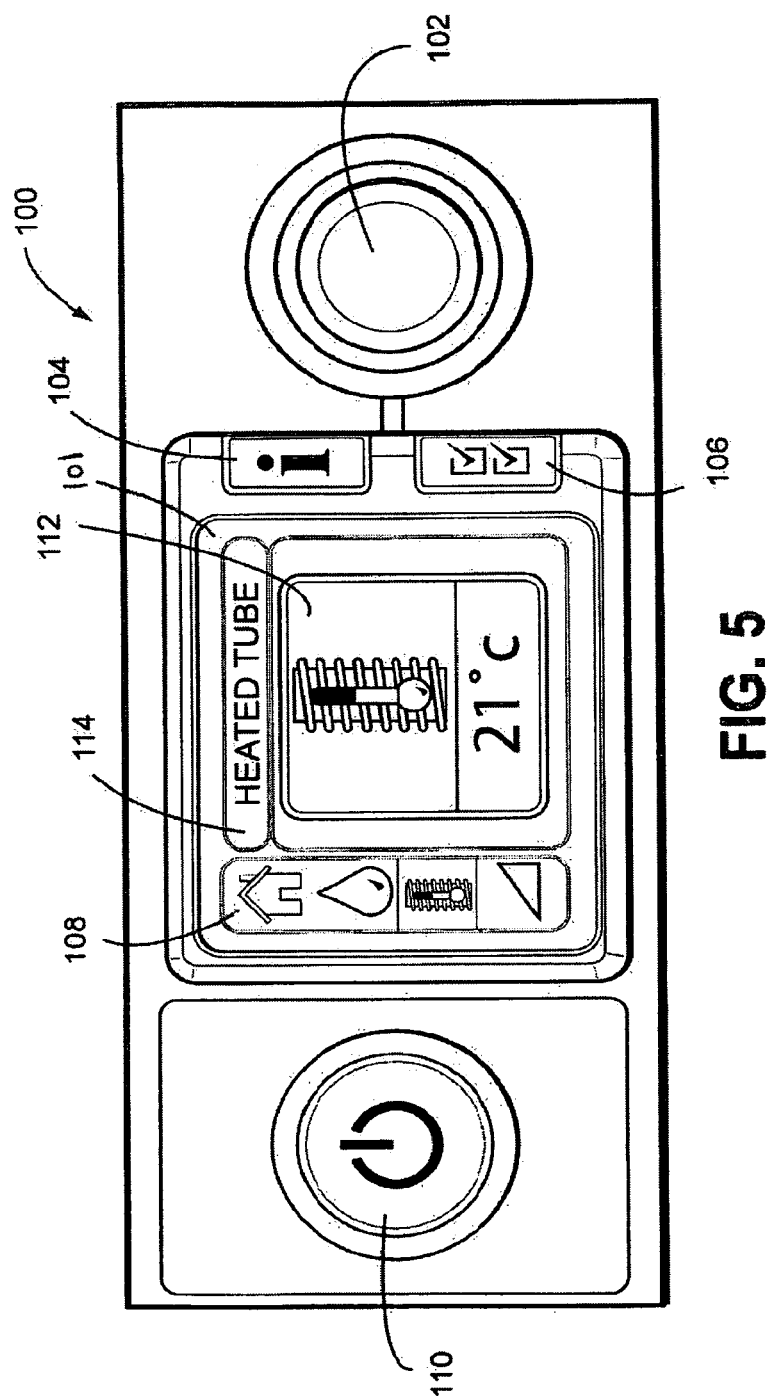
FIG. 5 shows an example layout of controls in accordance with another embodiment of the present technology.

FIG. 5 illustrates an example of a user interface (UI) 100 according to an alternative example. The UI 100 includes a display screen 101 (e.g., a color LCD window) as well as a control member 102, e.g., a rotatable push-button dial like the one described above. In one example, the display screen is 220 pixels×176 pixels, or larger. In one example, the display screen can show colours. In this example, the display screen and control member 102 are positioned adjacent one another, on a common face (e.g., top face) of the housing of the ventilator device.

UI 100 may include several other peripheral components adjacent the screen, such as menu keys (e.g., an information key 104 and a set up key 106), menu tabs 108, and an on/off button 110 which is positioned opposite from the control member 102. Screen may include a menu page 112 and a menu title 114. In one form, the UI may further comprise a humidifier indicator light.

Figure 6:
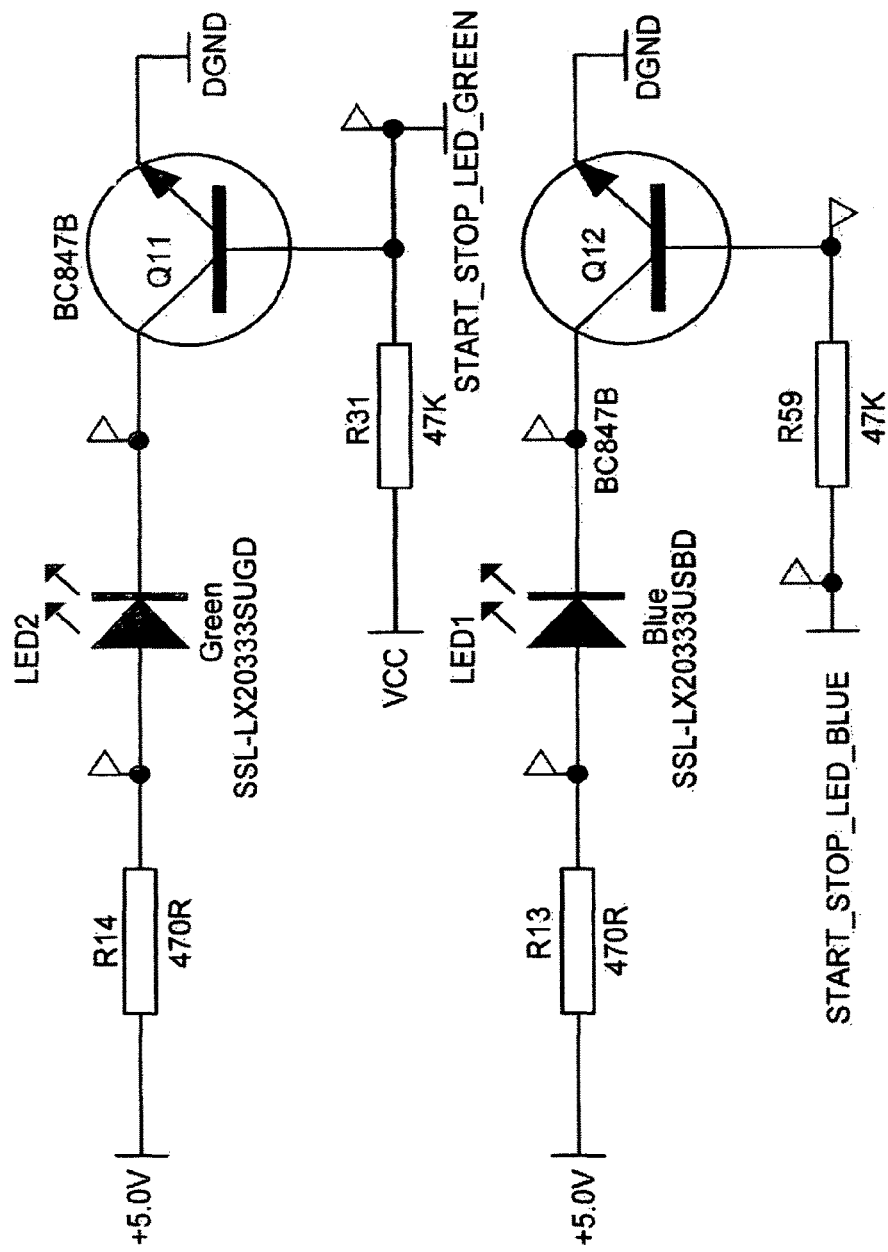
FIG. 6 shows a schematic of components relating to start/stop buttons in accordance with another embodiment of the present technology.
Figure 7:
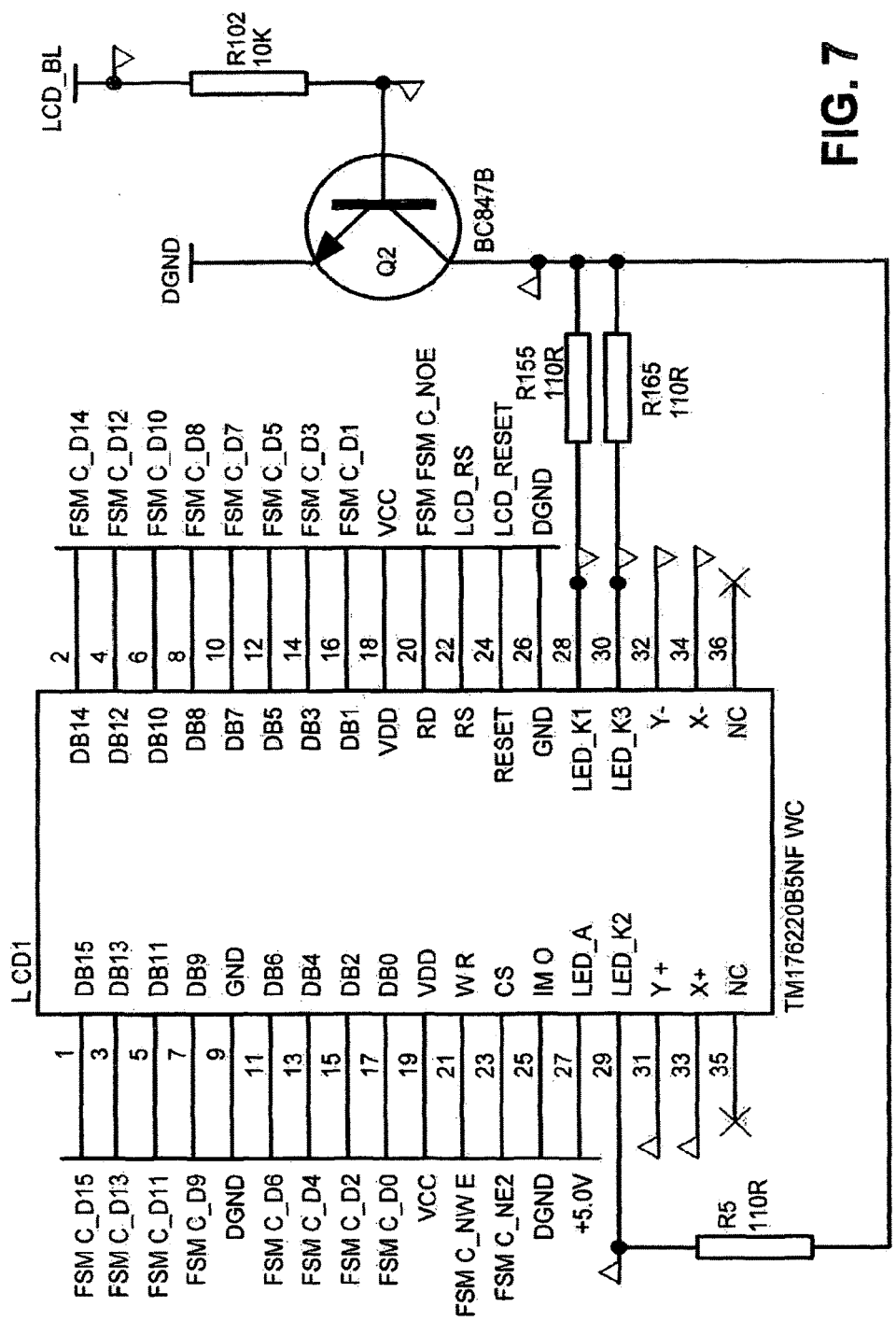
FIG. 7 shows a schematic of the components relating to the LCD display in accordance with another embodiment of the present technology.
Figure 8:
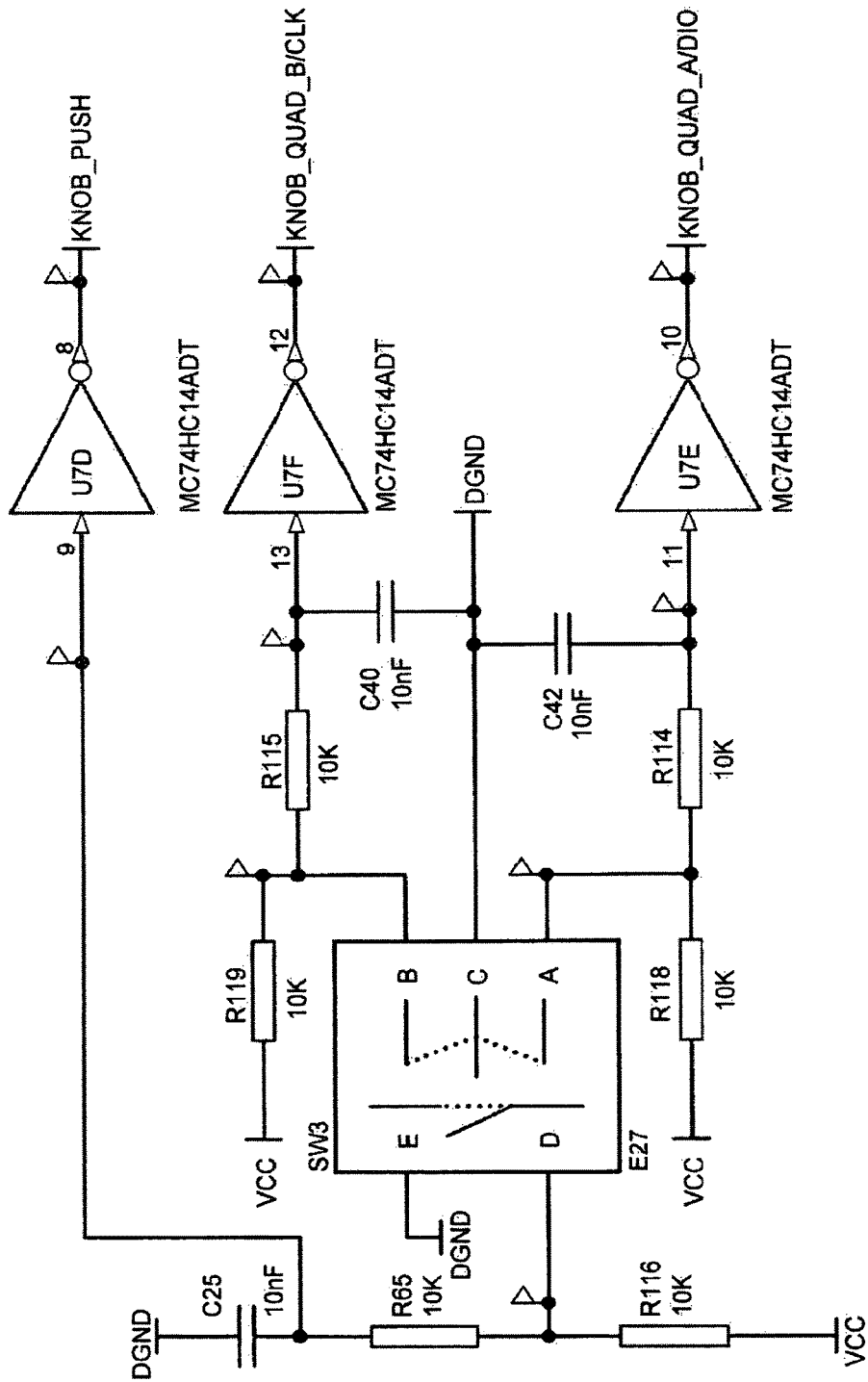
FIG. 8 shows a schematic of components relating to a control member, e.g., a push-button dial, in accordance with another embodiment of the present technology.
Figure 9:
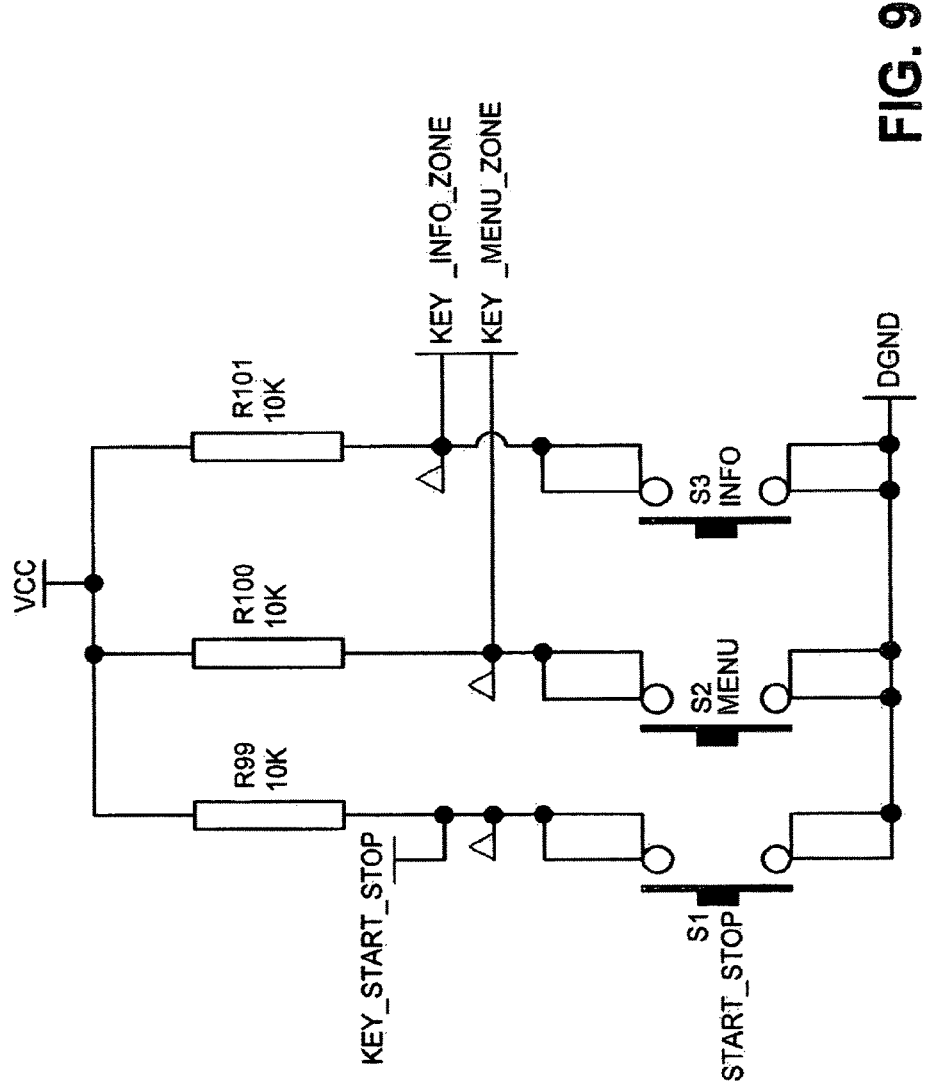
FIG. 9 shows a schematic of components relating to menu keys in accordance with another embodiment of the present technology.

Schematic diagrams of electrical circuits suitable for implementing the present technology are shown in FIG. 6 to FIG. 9, where FIG. 6 shows one example of components for the start/stop button, FIG. 7 shows one example of components for the display screen, FIG. 8 shows one example of components for the control member (e.g., rotatable push-button dial), and FIG. 9 shows one example of components relating to the menu keys. The circuits, which are examples, can be utilized in conjunction with the processor of the ventilator device.

Modes of Operation

The following preferred modes of operation are defined:

Standby mode: When the flow generator (FG) is not delivering pressure.

Mask Fitting mode: When the FG provides a set pressure that allows the user to check for leaks between the mask & face, and to adjust the fit of the mask to minimize them.

Run mode: Then FG is delivering pressure for the purpose of therapy (includes pressure ramping).

Error mode: When the FG has detected an error and is currently not delivering therapy.

User Interface States of Operation

The following user interface states of operation are defined:

No Power state: When the system has no mains power connected—either no power cord, a power cord with wall socket switched off, or a loss of mains power.

Power Save state: When the Start/Stop key has been pushed and held for over 3 seconds, and the UI has been switched off except for the dim green LED backlight of the Start/Stop Button.

Setup state: When a user is interacting with the user interface (UI) controls and the FG is in Standby Mode. Note: This is always the first state that the UI comes to when the Power is connected.

Adjust state: When a user is interacting with the UI controls and the FG is in Run Mode Warming Up state: When a user has activated the Warm Up function to pre-heat the humidifier (and optionally a heated tube) to the set value. The Warming Up state in this example can be stopped by selecting the Warming Up bar with the push button dial and pressing the dial to stop the Warming Up.

The Warming Up Function in this example may only be available when the Humidifier or Climate Control setting is greater than zero, however the warming up state will warm up both the humidifier and the heated tube to their set levels.

Warming Ready state: When the humidifier and heated tube have reached their settings and the system is ready for use. The system stays in this state until a 30 minute time out is reached (taken from the start of Warming Up). The Warming Ready state a be able to be stopped by selecting the Warming Ready bar with the push button dial and pressing the dial to stop the Warming Ready state.

Cool Down state: When the humidifier and heated tube have been in use during the Warming Up state, Warming Ready state, or Run mode, and the mode is changed to Standby Mode (eg pushing the Start/Stop button during Run mode, or stopping the Warm Up function). This state is maintained for a duration that allows the Humidifier to cool down. The purpose of this state is to minimise condensation build up in the system.

Idle state: When the user has not touched the controls for 2 minutes during Standby mode, the UI can "rest" with only the Start/Stop button illuminated and the LCD backlight faded to dim so that it is still readable.

In one example, this does not apply to the Warming Ready or Cool Down states.

Sleep state: When the user has not touched the controls for 2 minutes during Run mode, the UI can go to "sleep" with only the Start/Stop button illuminated.

In one example, this does not apply to the Mask Fit or Error states.

Mask Fit Standby state: Used when Mask Fit mode is activated from the Standby mode by pushing and holding the dial. If the user does not push anything, this state will time out after 3 minutes and will automatically bring the device to the Run Mode in the Adjust State.

Mask Fit Run state: Used when Mask Fit mode is activated from the Run mode by pushing and holding the dial. This is predominantly for patients, who wish to perform a Mask Fit, but have inadvertently activated Run mode via SmartStart when putting on their mask.

If the user does not push anything, this state will time out after 3 minutes and will automatically bring the device back to Run Mode in the Adjust State.

Alert state: Therapy continues and the UI displays an alert message over the Menu Page on the LCD and flashes a bright blue LED to indicate the alert state. Note: If the user alert has been disabled, the message will still appear but the LED will not flash.

The alert message and LED can be cleared by fixing the issue that caused the alert or they can be temporarily cleared when any key is pressed and normal navigation is resumed. If the issue that caused the alert is not fixed then the alert message will reappear after a time out period.

Two further states are specified—a patient menu state and a clinical menu state. In the clinical menu state, additional parameters are displayed and controllable when compared to the patient menu state. In addition, the parameters that are displayed and controllable in the patient menu are determined from the Clinical menu. For example, a clinician may decide that certain menus are available to one patient, and a different set of menus should be available for a different patient. In addition, the clinician can decide what information can be displayed for the patient during or after treatment.

For example, the clinician may decide whether to display such information as a "Sleep Quality Indicator" to the patient, and whether to display an Apnea Hypopnea Index (AHI).

While various preferred time intervals are specified, in other forms, other time intervals may be used.

Navigation

A control scheme for the present device comprises three main screens:

A home screen;
An information screen; and
A setup screen.

Each main screen includes at least one parameter. Where there is more than one parameter, turning the dial leads to each included parameter being highlighted in turn.

Whilst a parameter is highlighted, it may be selected by pressing the dial. Parameter adjustments may be made by rotating the dial. Parameter adjustments may be confirmed by pressing the dial.

In one example, the home screen is the default screen.

Pressing once on the first menu key results in the information screen being displayed.

Pressing a second time on the first menu key results in a return to the home screen.

Pressing once on the second menu key results in the setup screen being displayed.

Pressing a second time on the second menu key results in a return to the home screen.

In one form, the home screen displays information about a current patient treatment session.

From the home screen, selecting the information menu key once results in display of parameters defining the current treatment session, for example, CPAP pressure.

Selecting the information key once again, results in a return to the home screen. From the home screen, selecting the settings menu key once results in display of parameters that may be adjustable, for example, the ramp time. Selecting the settings key once again results in a return to the home screen.

The control scheme of the present device facilitates rapid navigation and display of patient treatment information, as well as facilitating adjustment of parameters where appropriate.

Backlighting

In one example form the start/stop button, the display and the humidifier indicator include backlighting. In another example form, certain colours are used, e.g., green, blue and orange. However other colours may be used. When a light changes state, the transition may be gradual, for example, over 3 seconds. In other forms, the transition may be more rapid, or slower, or instantaneous.

Start/Stop Button Backlighting:

In one example, when the device enters Power Save State the Start/Stop backlight can fade over 3 seconds to DIM GREEN.

In one example, when the device is "Ready for use", i.e., when it enters the Setup State, the Start/Stop backlight can fade over 3 seconds to BRIGHT GREEN.

In one example, when in the Standby Mode, and the UI is left for the Idle period, the Start/Stop backlight can remain BRIGHT GREEN.

In one example, when the device enters Warming Up, or Warming Ready States, the Start/Stop backlight can remain BRIGHT GREEN.

In one example, when the device enters the Cool Down State, from run mode the Start/Stop backlight can fade over 3 seconds to BRIGHT GREEN.

In one example, when going to Run Mode and delivering therapy, or entering the Mask Fit Run State, the Start/Stop backlight can be DIM BLUE within 0.5 seconds of entering this mode. The BLUE LED can remain DIM whilst in use unless there is an error, and then it can be BRIGHT BLUE FLASHING.

By providing the DIM BLUE light for run mode, and turning BRIGHT BLUE FLASHING only in event of error, the comfort of the patient and any bed partner is enhanced by not having a bright LED in the bedroom when trying to sleep.

Display Backlighting:

In one example, when the device enters Power Save State the LCD backlighting can fade over 3 seconds from ON to OFF.

In one example, when the device enters the Setup State, Adjust State, Mask Fitting State, or it is awakened from the Idle or Sleep states by pressing any keys or pressing/turning the Push Button Dial, the LCD backlighting can fade over 3 seconds from OFF to ON.

In one example, when the device enters the Warming Up, Warming Ready or Error State, the LCD backlight can be ON within 0.5 seconds of entering these States. In one example, when the device enters the Cool Down State, from run mode the LCD backlight can fade over 3 seconds to ON.

In one example, when in Standby mode and the UI is not interacted with for the Idle period, the LCD backlight can fade over 3 seconds to DIM.

In one example, when in Run mode and the UI is not interacted with for the Sleep period, the LCD backlight can fade over 3 seconds to OFF.

Fading of the device between the ON, DIM or OFF positions allows the patient's eyes to adjust to the change in brightness in the middle of the night when the device state is changed, for example if the patient wakes up the device or stops it to go to the toilet.

Fading to DIM during Standby mode will help save power, yet still provide some backlight for the patient to read the LCD display. Fading to OFF in the Run mode both saves power and minimises brightness in the bedroom, as during the Run mode the patient will have no need to read the LCD display.

Humidifier Backlight:

In one example, when the device enters the Power Save State the Humidifier Indicator backlight can fade over 3 seconds to OFF.

In one example, when the device enters the Setup State the Humidifier Indicator backlight can fade over 3 seconds to BRIGHT BLUE.

In one example, when the device enters the Mask Fit Standby State, the Humidifier Indicator backlight can remain the same as the state from which Mask Fit was activated from, and should return back to that state when Mask Fit is complete.

In one example, the Humidifier Indicator backlight can be BRIGHT BLUE within 0.5 seconds of entering the Error State with the Humidifier set to zero.

In one example, the Humidifier Indicator backlight can be BRIGHT ORANGE within 0.5 seconds of entering the Warming Ready, Cool Down or Error State with the Humidifier set between 0.5 and 6.

In one example, when the device enters the Warming Up State, the Humidifier Indicator backlight can fade over 3 seconds to DIM ORANGE.

In one example, when in the Standby or Run Mode, and the UI is left for the Idle or Sleep period, the Humidifier Indicator backlight can turn OFF.

In one example, when entering the Adjust State or Mask Fit Run State, the Humidifier Indicator backlight can fade over 3 seconds to either: a DIM ORANGE if either the Humidifier or Heated Tube are set between 0.5 and 6; or a DIM BLUE if both the Humidifier and Heated Tube are set to zero.

The above-described display and BRIGHT, DIM and OFF backlighting states, and the fading between them, are used for similar reasoning as described previously in relation to the Start/Stop button and Display backlighting.

Other Features

Automatic Mode Switching:

In one example, in Patient Run Mode—When there is no interaction with the UI for a waiting period of 30 seconds, the UI will automatically return to either, the Patient Climate Control, Humidifier Level, Heated Tube Level or Home Screen depending what is attached. This allows the patient to adjust their humidity or heated tube setting during the night without looking at the display.

In one form "no interaction" can include minor interaction. For example, the user interface may return to a Patient Climate Control mode in spite of a short period of interaction that may result from bumping or touching the user interface.

Whilst a period of 30 seconds is preferred for the required period, in other forms, other waiting periods may be used, such as about 5 seconds, or several minutes.

In one example, in Standby Mode—When there is no interaction with the UI for the Idle timeout duration, the UI will automatically exit the Patient Setup Menu and go to the Patient Home Screen in the Idle state.

In one example, during Run Mode in the Patient Menu, the UI will not allow the user to enter the Patient Info Menu.

In one form, when adjusting a numeric parameter, when the dial is turned slowly, it will adjust a parameter in minimal increments, eg 0.2 cmH$_2$O per encoder increment, but when the dial is turned quickly, it will adjust the parameter in whole number increments, eg 1.0 cm H$_2$O per encoder increment.

In a preferred form, the controls of the user interface are located on the flow generator. Hence some controls perform dual function of being able to control the humidifier as well as aspects of the flow generator. For example the dial may be able to control ramp time, pressure and humidification (including climate control level, heated tube temperature and humidity).

Battery

In a preferred embodiment the ventilator would include an internal battery. The battery may provide power supply for ventilation for a minimum of approximately 15 minutes but preferably longer, for example 30 minutes, 1 hour or 2 hours or longer. In one embodiment the battery may be charged or powered by an external DC input in the range of 12V to 28V. The battery may also be rechargeable using AC power. In another embodiment the ventilator may be adapted for use with an external battery. In one example, the external battery is rechargeable.

Hybrid Learn Mode

In another aspect of the invention the ventilator is adapted to learn the respiratory characteristics of a patient. The system incorporates the use of the bag valve mask system initially. The ventilator circuit includes a bag connection adapter for the bag-valve mask system to connect and/or disconnect such that initial ventilation is begun using the bag-valve mask through which sensors detect tidal volumes and pressures and feed this information into the ventilator device. After a set period of synchronisation, the mechanical ventilator takes over from the manual bag-valve mask system autonomously. In this manner the specific characteristics of the patient are not required to be entered into the system but are learnt during the initial manual ventilation with the bag valve mask system. In another embodiment the respiratory characteristics of the patient are learnt by the expiratory valve and the data transferred to the ventilator via a signal cable, data card or wireless transmission.

In one embodiment, the main benefit to the user is immediate administering of ventilation followed by immediate mechanical ventilation. This would negate or reduce the need for patient parameters, such as weight and age, to be entered into the system which are necessary for accurate tidal volumes and pressures to be given and also this would prevent lung injuries associated with mechanical ventilators. The bag-valve mask system allows the user to feel any resistance in the bag in order to prevent injury also.

In one embodiment the learn mode include as data storage module to enable the monitored patient respiratory characteristics to be recorded for later review. Furthermore, the device may include a communications module to facilitate the transfer of the stored data to other computer systems or devices, for example to the hospital or intensive care unit devices and/or systems. Such modules would provide effective transfer of the ventilation protocol and parameters between different systems.

The data recorded and logged by the system includes one or more of the following parameters: positive end expiratory pressure (PEEP) pressure, pressure support, minute ventilation, respiratory rate, tidal volume, inspiratory time, expiratory time, triggering events, cycling events, leak, spatial oxygen level, spatial carbon dioxide levels and pulse oximetry.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

Whilst the user interfaces in accordance with the present technology have been described with respect to ventilators, they are applicable to CPAP devices, controllers for CPAP devices and humidifiers for use with CPAP devices. The user interfaces of the present technology are particularly suitable for a home use respiratory device since they provide a more intuitive, convenient way of operating such devices for non-clinically trained people compared to more complicated prior art.

The invention claimed is:

1. A continuous positive airway pressure (CPAP) device to non-invasively treat a breathing disorder of a user, comprising:

a humidifier indicator backlight having an on state and an off state, a first backlit color and a second backlit color, and a first brightness and a second brightness, the humidifier indicator backlight configured to:
   indicate a plurality of user interface states of operation of a humidifier and/or a heated tube; and
   change between the on state and the off state, between the first backlit color and the second backlit color, and/or between the first brightness and the second brightness to indicate one of the plurality of user interface states of operation of the humidifier and/or the heated tube in response to user adjustment of a humidifier setting and/or a heated tube setting.

2. The CPAP device as claimed in claim 1, wherein the plurality of user interface states of operation includes a patient menu state and a clinical menu state,
   wherein more parameters are displayed and controllable in the clinical menu state relative to the patient menu state, and
   wherein the parameters that are displayed and controllable in the patient menu state are determined in the clinical menu state.

3. The CPAP device as claimed in claim 1, wherein each of the humidifier setting and the heated tube setting are independently adjustable.

4. The CPAP device as claimed in claim 1, wherein the first backlit color and the second backlit color are different colors, and
   wherein the first brightness and the second brightness are different.

5. The CPAP device as claimed in claim 1, further comprising a user input component configured to enable control of a ramp function in which a pressure level delivered to a patient is increased to a selected therapy pressure over a ramp time, said user input component having indicia thereon consisting of a ramp symbol.

6. The CPAP device as claimed in claim 1, wherein one of the first backlit color and the second backlit color is blue, and
   wherein the other of the first backlit color and the second backlit color is orange.

7. The CPAP device as claimed in claim 1, wherein the humidifier indicator backlight is configured to illuminate in the on state, the first backlit color, and the first brightness to indicate one of the plurality of user interface states of operation of the humidifier in response to user adjustment of the humidifier setting or the heated tube setting.

8. The CPAP device as claimed in claim 1, wherein the humidifier indicator backlight is configured to illuminate in the on state, the second backlit color, and the second brightness to indicate one of the plurality of user interface states of operation of the heated tube in response to user adjustment of the humidifier setting or the heated tube setting.

9. The CPAP device as claimed in claim 1, wherein the humidifier indicator backlight is configured to illuminate in the on state, the first backlit color, and the second brightness to indicate one of the plurality of user interface states of operation of the humidifier in response to user adjustment of the humidifier setting or the heated tube setting.

10. The CPAP device as claimed in claim 1, wherein the humidifier indicator backlight is configured to illuminate in the on state, the second backlit color, and the first brightness to indicate one of the plurality of user interface states of operation of the humidifier in response to user adjustment of the humidifier setting or the heated tube setting.

11. The CPAP device as claimed in claim 1, wherein the humidifier indicator backlight is configured to change to the off state to indicate one of the plurality of user interface states of operation of the humidifier in response to user adjustment of the humidifier setting or the heated tube setting.

12. The CPAP device as claimed in claim 1, further comprising a display screen, including a backlight, the display screen configured to display a plurality of CPAP device functions/modes and a plurality of parameters associated with at least one of said CPAP device functions/modes.

13. The CPAP device as claimed in claim 12, wherein the CPAP device functions/modes relate to one or more of the following:
   humidification settings, including climate control level;
   heated tube temperature;
   humidity; and
   flow generator settings, including pressure, patient type, patient weight, and treatment mode.

14. The CPAP device as claimed in claim 12, wherein the display screen is adapted to display a home screen, an information screen, and/or a setup screen.

15. The CPAP device as claimed in claim 14, wherein each of the home screen, the information screen, and the setup screen is a main screen that displays at least one of the parameters.

16. The CPAP device as claimed in claim 12, further comprising a finger-operable dial configured to select from the plurality of CPAP device functions/modes and parameters, the finger-operable dial being manipulatable in a first manner of manipulation to scroll between said parameters and being manipulatable in a second manner of manipulation to select one of the parameters.

17. The CPAP device as claimed in claim 16, further comprising a housing having a plurality of faces, the display screen, the finger-operable dial, and the humidifier indicator backlight all being located separately on a common face of the plurality of faces.

18. The CPAP device as claimed in claim 16, wherein the first manner of manipulation of the finger-operable dial includes rotation of the finger-operable dial, and
   wherein the second manner of manipulation of the finger-operable dial includes touching, pressing, and/or depression of the finger-operable dial.

19. The CPAP device as claimed in claim 16, further comprising a flow generator configured to deliver pressurized gas in the range of 2-30 cm $H_2O$.

20. The CPAP device as claimed in claim 19, wherein the plurality of CPAP device functions/modes includes at least two of the following:
   (i) a standby mode in which the flow generator is not delivering pressure;
   (ii) a run mode in which the flow generator is delivering pressure to provide therapy;
   (iii) an error mode in which the flow generator has detected an error and the flow generator is not delivering pressure; and
   (iv) a mask fitting mode in which the flow generator provides a set pressure to allow the user to check for leaks between a mask and the user's face and to adjust the fit of the mask to reduce the leaks.

21. The CPAP device as claimed in claim 19, wherein the finger-operable dial is located on the flow generator, and the finger-operable dial is configured to control the humidifier, the heated tube, and the flow generator.

22. The CPAP device as claimed in claim 20, wherein the display screen is configured to display one of the plurality of user interface states of operation.

23. The CPAP device as claimed in claim 22, further comprising controls for providing user input to the CPAP device,
wherein the plurality of user interface states of operation include at least one of the following:
(i) a no power state in which mains power is not connected to the CPAP device;
(ii) a power save state in which a start/stop key of the controls has been pushed and held by the user for more than 3 seconds, in which the display screen is off, and in which a start/stop key backlight is illuminated, the start/stop key backlight being configured to be illuminated in at least two different colors and at least two different levels of brightness;
(iii) a setup state in which the user is interacting with the controls of the CPAP device and in which the flow generator is in the standby mode;
(iv) an adjust state in which the user is interacting with the controls of the CPAP device and in which the flow generator is in the run mode;
(v) an idle state in which the flow generator is in the standby mode, in which the user has not touched the controls for at least 2 minutes, in which the start/stop key backlight is illuminated, and in which the backlight of the display screen is illuminated;
(vi) a sleep state in which the flow generator is in the run mode, in which the user has not touched the controls for at least 2 minutes, and in which only the start/stop key backlight is illuminated;
(viii) a mask fit standby state in which the mask fitting mode of the flow generator is activated from the standby mode by pushing and holding the finger-operable dial;
(ix) a mask fit run state in which the mask fitting mode of the flow generator is activated from the run mode by pushing and holding the finger-operable dial; and
(x) an alert state in which therapy is provided by the flow generator while the display screen displays an alert message and an LED is flashed.

24. A system to non-invasively treat a breathing disorder of a user, comprising:
the CPAP device as claimed in claim 23;
a removably attachable humidifier; and
a heated tube.

25. The system as claimed in claim 24, wherein the plurality of user interface states of operation further include at least one of the following:
(i) a warming up state in which a warm-up function has been activated to pre-heat the removably attachable humidifier to the humidifier setting and the heated tube to the heated tube setting;
(ii) a warming ready state in which the removably attachable humidifier has been pre-heated to the humidifier setting and the heated tube has been pre-heated to the heated tube setting; and
(iii) a cool down state in which the flow generator enters the standby mode after the removably attachable humidifier has been in use at the humidifier setting and the heated tube has been in use at the heated tube setting during the warming up state, during the warming ready state, or when the flow generator is in the run mode.

* * * * *